United States Patent [19]

Levinson

[11] Patent Number: 4,924,862

[45] Date of Patent: May 15, 1990

[54] PRESSURE CONTROLLER AND LEAK DETECTOR FOR TRACHEAL TUBE CUFF

[76] Inventor: Gary Levinson, 2 Oar Rd., Rowe, Mass. 01367

[21] Appl. No.: 87,154

[22] Filed: Aug. 19, 1987

[51] Int. Cl.$^5$ .................. A61M 16/00; A62B 9/02
[52] U.S. Cl. .................. 128/207.16; 128/202.22; 128/205.23; 128/205.24
[58] Field of Search .................. 128/204.25, 207.16, 128/205.24, 202.22, 207.14, 207.15, 205.23

[56] References Cited

U.S. PATENT DOCUMENTS

| | | | |
|---|---|---|---|
| 3,682,166 | 8/1972 | Jacobs | 128/145.8 |
| 3,794,026 | 2/1974 | Jacobs | 128/207.15 |
| 3,931,822 | 1/1976 | Marici | 128/351 |
| 4,020,849 | 5/1977 | Jackson | 128/351 |
| 4,090,518 | 5/1978 | Elam | 128/349 B |
| 4,116,201 | 9/1978 | Shah | 128/351 |
| 4,119,101 | 10/1978 | Igrich | 128/351 |
| 4,134,407 | 1/1979 | Elam | 128/207.15 |
| 4,147,170 | 4/1979 | Taylor | 128/349 BV |
| 4,159,722 | 7/1979 | Walker | 137/496 |
| 4,178,940 | 12/1979 | Au | 128/207.15 |
| 4,224,939 | 9/1980 | Lang | 128/205.13 |
| 4,256,099 | 3/1981 | Dryden | 128/200.26 |
| 4,285,340 | 8/1981 | Gezari et al. | 128/205.24 |
| 4,316,458 | 2/1982 | Hammerton-Fraser | 128/205.24 |
| 4,383,534 | 5/1983 | Peters | 128/671 |
| 4,471,775 | 9/1984 | Clair et al. | 128/205.24 |
| 4,501,273 | 2/1985 | McGinnis | 128/207.15 |
| 4,519,388 | 5/1985 | Schwanbom et al. | 128/204.25 |
| 4,520,812 | 6/1985 | Freitag et al. | 128/204.25 |
| 4,526,196 | 7/1985 | Pistillo | 137/557 |
| 4,565,194 | 1/1986 | Weerda et al. | 128/204.23 |
| 4,573,462 | 3/1986 | Baum | 128/204.25 |
| 4,583,917 | 4/1986 | Shah | 417/63 |
| 4,617,015 | 10/1986 | Foltz | 604/100 |
| 4,630,606 | 12/1986 | Weerda et al. | 128/207.14 |
| 4,644,947 | 2/1987 | Whitwan et al. | 128/207.16 |
| 4,646,733 | 3/1987 | Stroh et al. | 128/207.16 |
| 4,649,914 | 3/1987 | Kowaleski | 128/207.15 |

*Primary Examiner*—A. Michael Chambers
*Attorney, Agent, or Firm*—Fish & Richardson

[57] ABSTRACT

An inflation control system for the cuff of a tracheal tube includes an adjustable pressure relief valve with an inlet and an outlet connected in series between the cuff and a source of pressurized gas, and a valved exhaust port urged toward the closed condition. When the tracheal tube is connected to an exhalation valve and a volume ventilator with a pulsed exhalation valve drive line, two relief valves are preferred: a low pressure valve in series with a high pressure valve. The low pressure relief valve is controlled by the exhalation drive line, preferably by means of an inflatable balloon in communication with the exhalation drive line. A flow detector in the cuff inflation line produces an electrical output signal indicative of airflow to activate an alarm signifying a continuous airflow condition due to cuff leak. The airflow detector preferably includes a mechanical flow meter in combination with a photoelectric sensor.

20 Claims, 3 Drawing Sheets

PRESSURE CONTROLLER AND LEAK DETECTOR FOR TRACHEAL TUBE CUFF

BACKGROUND OF THE INVENTION

The invention relates to the controlled inflation of balloon cuffs which surround the end of tracheal tubes used in respiratory medicine. Tracheal tubes include both tracheostomy and endotracheal tubes. An endotracheal tube is one which can quickly be inserted through the mouth or nose into the trachea, while a tracheostomy tube must be inserted through a surgical opening in the neck. However, for the purposes of this invention, they may be viewed as the same, and will therefore herein be referred to collectively as tracheal tubes, unless otherwise stated.

Tracheal tubes may be inserted for a variety of reasons, including, the need for mechanical ventilation, bypass of an obstruction, removal of secretions, easier ventilation due to less dead space. In most circumstances, it is necessary to seal the outside of the tracheal tube to the inner tracheal lining, i.e., the tracheal mucosa. During mechanical ventilation this is particularly true, since a closed circuit is necessary for a ventilator to force a given volume of air or oxygen under pressure into a patient's lungs. When a patient is not being mechanically ventilated, a seal may or may not be required. In this situation, the need for a seal will generally depend on whether or not there is a risk of aspiration. In the case of an endotracheal tube, this risk is always present, while with a tracheostomy tube, this risk is often present. Therefore, most patients require a seal either to prevent aspiration or to create a closed circuit for mechanical ventilation. Because of the pressurization of the system, a tighter seal is necessary during mechanical ventilation than is necessary to prevent aspiration in the absence of mechanical ventilation.

It is well known that over pressurization of the tracheal cuff can cause significant tracheal damage including, hemorrhage, ulcers, perforation, and strictures. It is generally accepted that the main cause of this damage is occlusion of blood vessels leading to loss of blood flow with resultant necrosis of the tracheal lining. Experience has shown that an intra cuff pressure of less than 25 cm $H_2O$ is associated with significantly fewer complications. This is consistent with experimental data suggesting that the capillary perfusion pressure in the tracheal mucosa is in the range of 30–40 cm $H_2O$. Thus, a cuff pressure of 25 cm $H_2O$ would still allow some blood flow. However, the numbers noted above are not absolute. Damage is occasionally seen with cuff pressures of 25 cm $H_2O$ because perfusion pressures may be lower than expected due, for example, to low blood pressure. Therefore, the best approach is to use the lowest cuff pressure consistent with an adequate ventilation seal and the prevention of aspiration.

Tracheal cuffs are frequently positional, that is, as the patient moves, the balloon moves into tighter and looser positions within the trachea. This causes the pressure in the cuff to increase and decrease respectively. The result is too much pressure on the mucosa or a pressure leak, respectively. The problem of tracheal tube movement is not just a theoretical one. The phrases "positional tube" or "positional cuff" are ones frequently heard in practice to report a condition in which, after proper inflation of a cuff, movement of the patient causes excessive, often audible leakage of the ventilator volume around the cuff. In this case, the patient's lungs fail to receive the prescribed volume. Positional cuff occurring during the exhalation phase has the attendant risk of aspiration. The same kind of risk is presented by positional cuff where a tracheal tube is used without a volume ventilator, for example, in a tracheostomy. There is a further way in which deflation can occur: through a leak in the balloon cuff itself or in the cuff inflation line.

SUMMARY OF THE INVENTION

A general feature of the invention is a bidirectional, continuous inflation control system for a tracheal tube cuff including a pressure relief valve having an inlet, an outlet and an exhaust port urged toward the closed condition, and a cuff inflation line connecting the inlet and outlet of the relief valve in series between the cuff and a source of pressurized gas.

When the tracheal tube is to be connected to a volume ventilator, two pressure relief valves are preferred: a low pressure valve in series with a high pressure valve in the cuff inflation line. Each valve has an inlet and an outlet and a valved exhaust port urged toward the closed condition, the high pressure valve requiring higher pressure in the cuff inflation line to open the exhaust port than the low pressure valve. The inlets and outlets of both valves are connected in series in the cuff inflation line. This arrangement offers the capability of adjusting the pressure in the cuff according to either of two limits while continuously maintaining the ability to supply additional volume to the cuff. Thus, during inhalation, the cuff pressure can be regulated by the setting of the higher pressure relief valve by, in effect, disabling the low pressure relief valve.

When the tracheal tube is connected to a volume ventilator having an exhalation valve drive line, another feature of the invention is brought into play by connecting an adjustable pressure relief valve in series between the cuff and a source of pressurized gas and using the exhalation drive line to actuate a mechanism for blocking the exhaust port on the pressure relief valve whenever the exhalation valve is closed. Preferred embodiments of the invention include an inflatable balloon in gaseous communication with the exhalation drive line for sealing off the exhaust port of the pressure relief valve when inflated. In addition, a three-way valve connects the balloon to (1) the exhalation drive line, (2) a source of pressurized gas or (3) the atmosphere.

A generally preferred mode of operation, and another feature of the invention, is to employ the aforementioned pressure relief valve as a low pressure relief valve in series with an adjustable high pressure relief valve having a valved exhaust port urged closed requiring higher pressure to open than the exhaust port of the low pressure valve. In the preferred embodiment, the low and high pressure valves are both magnetic PEEP type valves as hereinafter described.

A further general feature of the invention is to monitor cuff leakage by means of a flow detector which produces an electrical output signal indicative of airflow in the cuff inflation line. An alarm circuit connected to the output of the detector signals an alarm when an airflow condition is continuously detected for a predetermined length of time. Preferred embodiments of this feature of the invention include the use of a mechanical flow meter in series with the cuff inflation line along with a sensor connected to the flow meter to produce the electrical output signal.

The features of the invention provide monitored, automatic bidirectional pressure control of the tracheal tube cuff during both respiratory phases, as well as cuff leak protection.

Other advantages and features will become apparent from the following description of the preferred embodiments and from the claims.

DESCRIPTION OF THE PREFERRED EMBODIMENT

The drawings are briefly described as follows.

STRUCTURE

Figure 1:
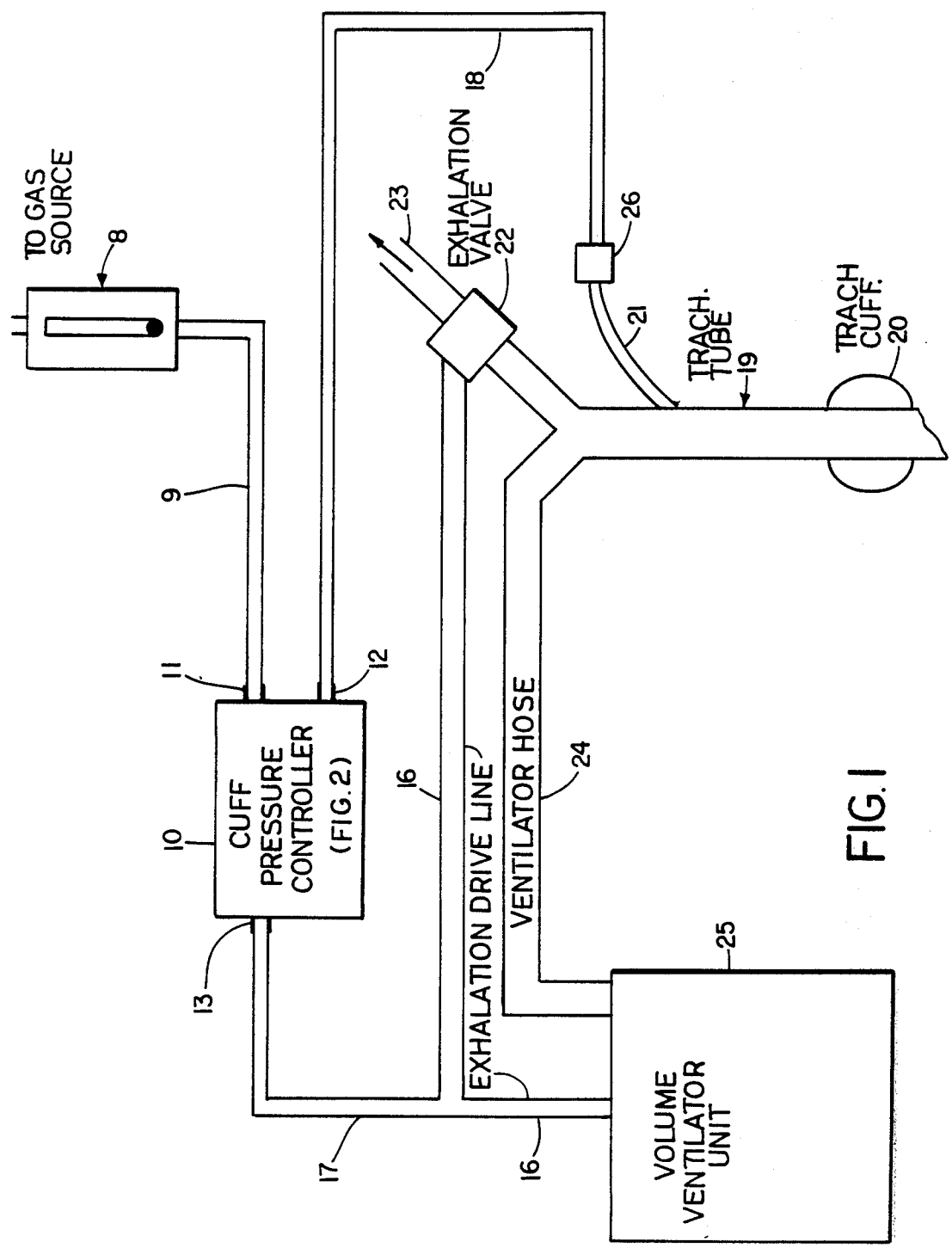
FIG. 1 is a schematic diagram of the cuff pressure controller and its external connections to a conventional ventilator, tracheal tube, and exhalation valve.

FIG. 1 indicates the three external pneumatic connections to the cuff pressure controller 10 (hereafter referred to as the controller). The controller operates on either air or oxygen at low input flow rates of around 1 liter per minute. Hose fitting 11 is connected to a source of oxygen or air via a standard rotameter type flow meter 8 and hose 9. Hose fitting 13 on controller 10 is connected to the ventilator exhalation valve drive line 16 via hose 17. This connection allows the controller 10 to utilize the exhalation drive line pressure pulse during inhalation. However, this connection is only necessary when the controller is used in the pulse mode. Fitting 12 is connected to the tracheal cuff 20 via hose 18, connector 26, and conventional pilot tube 21. Connector 26 and pilot tube 21 are part of the tracheal tube 19 itself. The pilot tube is ordinarily formed in the wall of the tracheal tube 19 and extends axially to a port inside the doughnut-shaped inflatable cuff bonded around the distal end of the tracheal tube. Flow meter 8 is adjusted to supply a flow of about 1 liter per minute.

When the ventilator 25 begins an inhalation, two things occur simultaneously: a given volume of air/oxygen flows through hose 24 into the tracheal tube 19, and pressurized gas flows into exhalation valve 22 via hose 16. This closes exhalation valve 22 so that the volume of air/oxygen entering the tracheal tube 19 cannot be exhausted out of the expiratory tubing 23. The tracheal tube cuff 20 is pressurized via the controller 10 to prevent leakage of the volume of air/oxygen around the tracheal tube 19.

During exhalation the ventilator 25 simultaneously vents line 16 and stops supplying the volume of air/oxygen to tubing 24. The venting causes relaxation of the exhalation valve 22, allowing the previously inspired volume of air/oxygen to be exhaled by the patient through tracheal tube 19, exhalation valve 22 and expiratory tubing 23.

Positive end expiratory pressure (PEEP) valves are normally used to apply PEEP to a patient's lungs in order to improve oxygenation. They provide back pressure or "resistance" to exhalation so as to maintain therapeutic pressure on the lungs. Thus, it is not uncommon to find a PEEP valve with just an inlet and an exhaust port in the expiratory tubing line 23.

Figure 2:
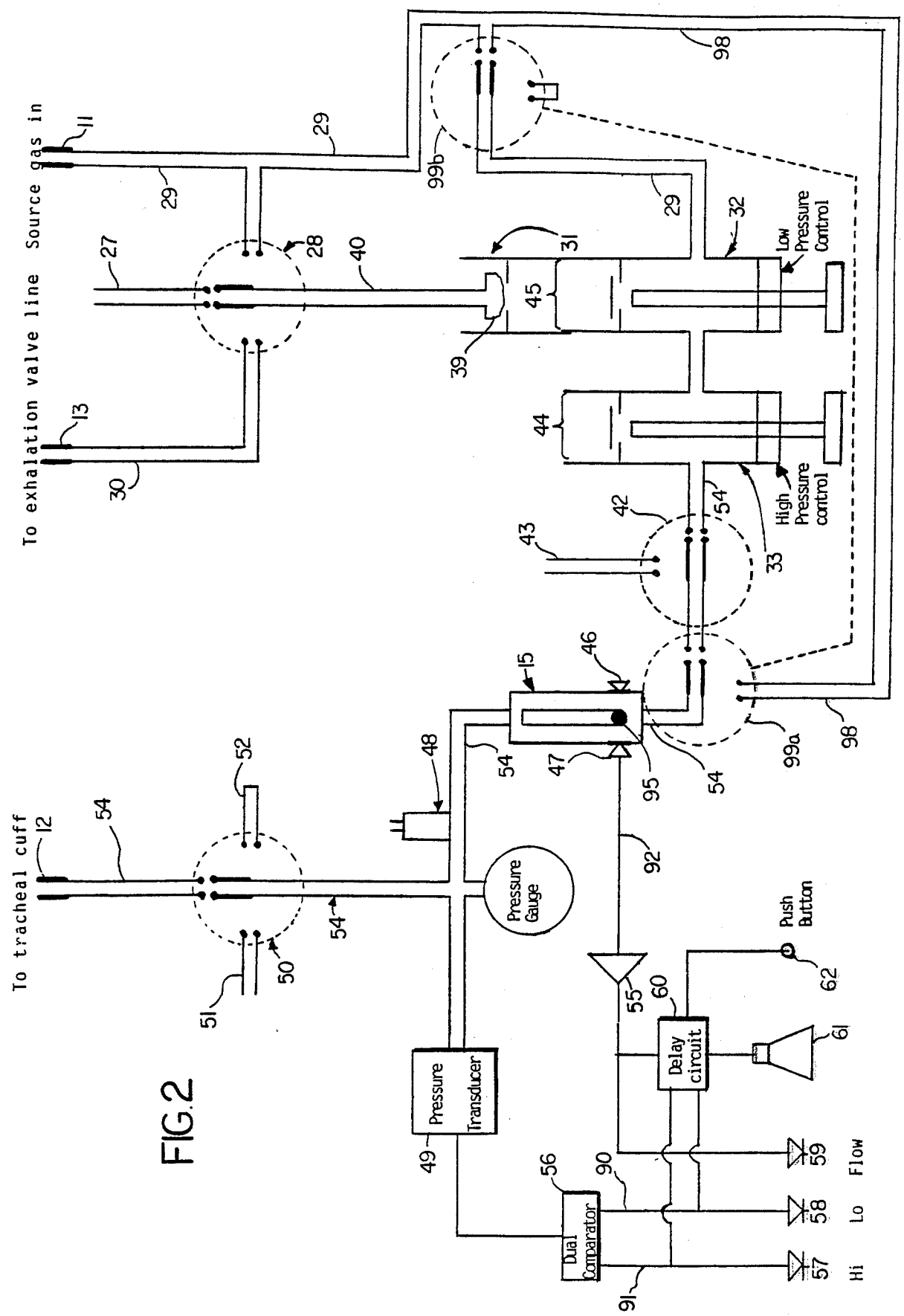
FIG. 2 is a schematic diagram of the internal pneumatic and electrical design of the cuff pressure controller of FIG. 1.

As shown in FIG. 2, a pair of modified PEEP-type valves 32 and 33 are employed in a different way in the cuff pressure controller. In essence these valves are adjustable relief valves, since they maintain their pressure by actually releasing or bleeding off volume when the preset pressure is exceeded. Unlike the conventional usage in the expiratory line, here the PEEP type valves are connected with inlets and outlets in series with the cuff inflation line. Because of the bi-directional nature of this control system, the pressures will always be set at exactly the preset point whether the cuff pressure begins above or below that point. The PEEP valves thus can instantaneously either supply extra volume to, or accept extra volume from the cuff. Either magnetic or spring-loaded PEEP valves may be used, though the design herein described uses magnetic ones, for example, of the type manufactured by Instrumentation Industries, Inc. of Bethal Park, Pennsylvania.

Figure 3:
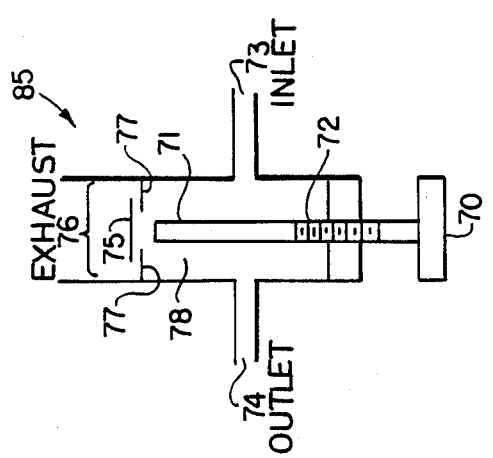
FIG. 3 is a sectional view of a PEEP valve of the type employed in the controller of FIG. 2.

FIG. 3 shows the functional design of a magnetic PEEP valve as applied to the controller 10. Air or oxygen enters port 73 at a rate of about 1 liter per minute and at a high pressure. Knob 70 turns magnet 71 via threads 72 closer to or further from diaphragm 75. Diaphragm 75 is usually ferrous metal embedded in rubber. The closer magnet 71 is to the diaphragm 75, the tighter the diaphragm 75 is pulled against orifice flange 77, and the greater the pressure needed to unseat the diaphragm 75. When the pressure in chamber 78 reaches the preset point determined by the position of magnet 71, the excess pressure unseats diaphragm 75 and air exhausts out port 76. Port 74 ultimately connects to the tracheal cuff. Once the system is pressurized, there is usually no net flow out port 74. Therefore, the pressure in chamber 78 is equal to that of the cuff. If the cuff pressure falls, chamber 78 will supply just enough volume to port 74 from inlet 73 to equalize the pressure in the cuff to that of chamber 78. If the cuff pressure rises, chamber 78 will accept extra volume from port 74 and exhaust it out port 76 until the pressure in the cuff is equalized to that of chamber 78.

Figure 4:
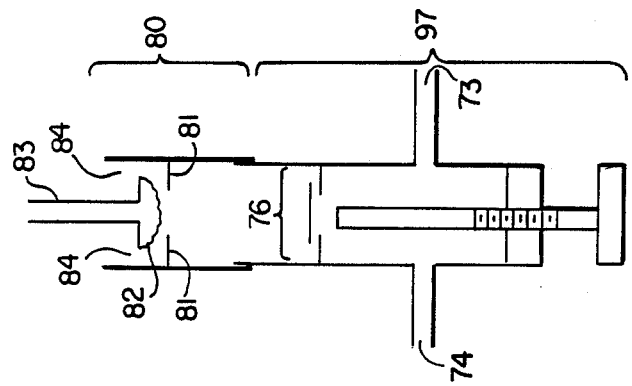
FIG. 4 is a sectional view of an exhalation valve mounted on the exhaust port of a PEEP valve as employed in the controller of FIG. 2.

FIG. 4 shows an exhalation valve 80 connected to the exhaust port 76 of a PEEP valve 97. This exhalation valve 80 is similar to the ventilator exhalation valve 22 shown in FIG. 1. As described under FIG. 3, normally the excess flow is exhausted out port 76. In FIG. 4, this excess flow is exhausted out port 76 and then through exhalation valve 80, and out port 84. However, when line 83 is pressurized, balloon 82 is inflated against orifice flange 81. This prevents excess flow from exhausting out port 76. In this situation, the PEEP valve 97 becomes nonfunctional, and flow entering port 73 flows out port 74.

Returning to FIG. 2, the operation of the controller 10 will be described. Source gas at 1 liter per minute is attached to hose fitting 11 and passes through tube 29 via valve 99b to PEEP valve 32. (Valves 99b and 99a comprise a single momentary pushbutton valve which is shown in its normal rest position in FIG. 2 to be explained under the alarm system,) PEEP valve 32 is connected in series with PEEP valve 33. PEEP valve 32 is adjustable from 0-35 cm $H_2O$ pressure, while PEEP valve 33 is adjustable from 0-75 cm $H_2O$ pressure. PEEP valve 33 should always be set at a higher pressure than that of PEEP valve 32. Therefore, normally low pressure PEEP valve 32 will determine the system pressure which will be reflected in the tracheal cuff by communication through PEEP valve 33 and tube 54. However, when balloon 39 in exhalation valve 31 is inflated, PEEP valve 32 will become nonfunctional and the system pressure will be determined by high pressure PEEP valve 33.

Balloon 39 is connected via tube 40 to a manual 3-way ball valve 2B. By turning ball valve 28, the balloon 39 can be connected to pressure line 29, can be vented to the atmosphere via tube 27, or can be connected to the ventilator's exhalation valve drive line via tube 30 and external hose connector 13. In this latter position, the balloon 39 will inflate each time the ventilator cycles into the inhalation phase in which air volume is pumped into the lungs. Therefore, during inhalation, cuff pressure will be determined by high pressure PEEP valve 33 while during exhalation cuff pressure will be determined by low pressure PEEP valve 32. When balloon 39 is vented to the atmosphere, PEEP valve 32 will continuously determine the cuff pressure. When balloon 39 is connected to pressure line 29 by valve 28, PEEP valve 33 will continuously determine the cuff pressure. Thus, the tracheal cuff can be controlled with continuous low pressure for most situations, continuous high pressure for emergencies, or pulse pressure. Pulse pressure is useful when a seal in the trachea cannot be maintained with continuous low pressure. This is apt to occur in mechanically ventilated patients with stiff lungs when high pressures are required to force the air/oxygen mixture into the tracheal tube (19, FIG. 1).

The pressure in the PEEP valves 32 and 33 will be communicated to the tracheal cuff via tube 54. This pressure will be communicated through momentary pushbutton valves 42 and 99a (both shown in FIG. 2 in their at rest positions—to be explained under the alarm system), flow meter 15, 3-way ball valve 50 (to be explained under the alarm system), and out hose fitting 12 to the tracheal cuff.

Flow meter 15 is another unique design feature of the controller. Normally there will not be continuous flow through tube 54. There will normally be intermittent flow through tube 54 when the controller 10 is first hooked up to the tracheal cuff, if the tracheal cuff moves to a looser position within the patient's trachea, and during pulse operation. However, if the cuff develops a leak, there will be continuous flow through tube 54 into the tracheal cuff. This flow will be indicated on the flow meter 15 which will measure extremely low flows in a range of 5-100 cc's per minute. The flow meter will accomplish two objectives: (1) it will indicate the presence of a cuff leak, and (2) it will give a relative index of the size of the cuff leak. A third function relating to cuff leak is carried out by the series connected PEEP valves, namely maintaining cuff pressure despite a slow leak. This latter objective will allow an interval of time for the users to change the tracheal tube (19, FIG. 1) before an emergency situation occurs in which the patient cannot be ventilated due to loss of tracheal cuff seal. In the embodiment of the invention herein described, a rotameter is used to indicate cuff leak because of its simplicity, reliability, and the availability of extremely low flow rotameters. However, other flow meters such as pneumotachometers and mass flow meters can be used.

Pressure gauge 14 is connected to tube 54 and therefore will indicate tracheal cuff pressure. Pressure adjustments are made via this gauge. An internal emergency pressure relief valve 48 is set at 80 cm $H_2O$ as a safety valve.

Alarm System

The alarm system monitors three parameters: (1) low pressure, (2) high pressure, and (3) cuff leak. An abnormal condition in any one of these parameters is indicated by an audible alarm from tweeter 61 (FIG. 2). In addition, there are three LEDs, 57, 58 and 59, which indicate which of the three parameters are abnormal. The LEDs will reflect momentary changes in the three parameters and therefore will normally flash periodically. This is true in the case of flow as described above. But it is also true, in the case of the high pressure LED 57, when the controller 10 is used in the pulse pressure mode. This is because the high pressure pulse as determined by PEEP valve 33 will usually be above the set point of the high pressure alarm. The low pressure LED 58 might flash during tracheal tube movement. However, the tweeter 61 will be connected to a multiple time delay circuit 60 such that an audible alarm will be emitted only after a continuous signal of greater than 15 seconds occurs, indicating a true fault.

The controller 10 contains two fault sensing systems: one for high and low pressure and one for cuff leak. Pressure transducer 49 is connected to tube 54, and therefore reflects the cuff pressure. The transducer 49 puts out a voltage which varies depending on the pressure in tube 54. Dual comparator circuit 56 continuously senses the voltage output from transducer 49. If the voltage falls below a predetermined point, a signal flows through wire 90, lighting LED 58 and starting time delay 60. If the voltage rises above a predetermined point, a signal flows through wire 91, lighting LED 57 and starting time delay 60. If either of these two conditions exists for more than 15 seconds, the tweeter 61 will sound. If either of these two conditions terminates before 15 seconds, the respective LED 57 or 58 will go out and the respective timer will reset itself.

Cuff leak is sensed by a photoelectric circuit on the flow meter (rotameter) 15. On one side of the rotameter 15, there is an LED 46 or other light source which is continuously lit. On the other side of the rotameter 15, there is phototransistor 47 or other light sensor. The LED 46 and the phototransistor 47 are positioned such that when the float 95 of rotameter 15 is in its rest position, indicating no flow, the light from LED 46 is blocked from hitting phototransistor 47 by float 95. Therefore, in the no cuff leak condition, phototransistor 47 will sense no light. If there is flow through rotameter 15, float 95 will rise off its rest position allowing light from LED 46 to hit phototransistor 47. Therefore, in a cuff leak condition, phototransistor 47 will sense light and send a signal via wire 92 to amplifier 55, which will in turn send a signal via wire 93 which will light LED 59 and turn on time delay 60. If flow through rotameter 15 continues for greater than 15 seconds, tweeter 61 will sound. If flow through rotameter 15 terminates within 15 seconds, LED 59 will go out and the respective time delay 60 will reset.

The alarm check system will now be described. Alarms are checked by actually creating a fault, rather than by just checking the electrical circuit. This will therefore check the mechanical as well as the electrical components. To make a cuff leak alarm check, ball valve 50 is turned to tube 51, which is vented to the atmosphere. This allows continuous flow through tube 54 and rotameter 15. This should turn on LED 59 immediately and tweeter 61 in 15 seconds. To make a high pressure alarm check, ball valve 50 is turned to tube 52, which is closed. Then momentary pushbutton valve 99a–99b is pressed. This action will cause pressurized source gas in hose 29 to bypass PEEP valves 32 and 33 and enter hose 54. The pressure in hose 54 will then rise to 80 cm H₂O as determined by internal pressure release valve 48. When the high pressure test is performed, LED 57 should light immediately and tweeter 61 should sound in 15 seconds. In addition, the high pressure test will check the function of pressure release valve 48 by confirming that the system pressure becomes 80 cm H₂O. When valve 99a–99b is let go it assumes its normal flow through position as indicated in FIG. 2.

To make a low pressure alarm check, ball valve 50 is turned to tube 52, which is closed. Then momentary pushbutton valve 42 is pressed so that tube 54 is connected to tube 43, which is vented to the atmosphere. This action depressurizes tube 54 between valve 42 and ball valve 50. When this test is performed, LED 58 should light immediately and tweeter 61 should sound in 15 seconds. When valve 42 is let go it assumes its normal flow through position as indicated in FIG. 2. Ball valve 50 is designed such that when it is switched either to tube 51 or 52, the tracheal cuff remains pressurized because it will not leak back into ball valve 50.

The system also has a manually operated time delay. Push button 62 activates a separate circuit in time delay 60. When pushed it turns off tweeter 61 for two minutes. This button is used to silence the tweeter when troubleshooting a fault, or when the continuous high pressure mode is used during emergencies.

The system of the foregoing description has the advantage of offering flexible operation with automatic bidirectional control of the cuff inflation line. The controller takes advantage of the preexisting exhalation valve drive line designed for proper inflation of the conventional exhalation valve by adding a second exhalation type valve in parallel which may advantageously be virtually identical to the regular balloon occluder type exhalation valve. The use of a low pressure PEEP type valve in series with the high pressure PEEP type valve insures that the controller is capable of adding volume to the cuff in either respiratory phase. In addition, because the cuff line is always connected to the source, volume can be continuously supplied if there is a leak, irrespective of the respiratory phase. The use of a flow meter in the cuff line makes possible positive analog indication of flow level as well as an alarm signal by means of a simple electrical sensor irrespective of cuff line pressure.

The specific implementation of the system given here is only by way of illustration. Other embodiments are within the claims.

I claim:

1. An inflation control system for an inflatable cuff of a tracheal tube connected to a ventilator having alternating inspiration and exhalation cycles, comprising
    an adjustable low pressure relief valve having an inlet and an outlet and a valved exhaust port urged toward the closed condition,
    an adjustable high pressure relief valve having an inlet and an outlet and a valved exhaust port urged toward the closed condition requiring higher pressure to open than said exhaust port of said low pressure valve, and
    a cuff inflation line substantially continuously connecting the respective inlets and outlets of said low and high pressure valves in series between the cuff and a substantially continuous source of pressurized gas throughout inspiration and exhalation cycles of said ventilator.

2. The system of claim 1, wherein said high and low pressure valves are magnetic PEEP type valves.

3. The system of claim 1, further comprising
    a flow detector for producing an electrical output signal indicative of airflow in said cuff inflation line, and
    an alarm circuit connected to the output of said flow detector for producing an alarm indication if a continuous airflow condition indicative of a cuff leak is detected.

4. The system of claim 3, wherein said flow detector includes a mechanical flow meter in series with said cuff inflation line and sensor means operatively connected to said flowmeter for producing an electrical output signal indicative of airflow in said cuff inflation line.

5. The system of claim 1, further comprising means responsive to cycling of the ventilator for locking the exhaust port on the low pressure valve closed during the inspiration cycle.

6. An inflation control system for an inflatable cuff of a tracheal tube connected to a exhalation valve and a volume ventilator having alternating inspiration and exhalation cycles and a pulsed exhalation valve drive line, comprising
    an adjustable low pressure relief valve having an inlet and an outlet and a valved exhaust port urged toward the closed condition,
    means responsive to said exhalation drive line for locking the exhaust port on the low pressure valve closed,
    an adjustable high pressure relief valve having an inlet and an outlet and a valved exhaust port urged toward the closed condition requiring higher pressure to open than said exhaust port of said low pressure valve, and
    a cuff inflation line substantially continuously connecting the respective inlets and outlets of said low and high pressure valves in series between the cuff and a source of pressurized gas throughout the inspiration and exhalation cycles of said ventilator.

7. The system of claim 6, wherein said high and low pressure valves are magnetic PREP-type valves.

8. The system of claim 6, wherein said locking means includes means for temporarily blocking said exhaust port of said low pressure relief valve.

9. The system of claim 8, wherein said blocking means includes an inflatable balloon in gaseous communication with the exhalation drive line for sealing off the exhaust port of the low pressure valve when inflated in the same manner as the exhalation valve.

10. The system of claim 9, further comprising a manual 3-way valve connecting said balloon to (1) said exhalation drive line, (2) a source of pressurized gas or (3) the atmosphere.

11. The system of claim 6, further comprising
    a flow detector for producing an electrical output signal indicative of airflow in said cuff inflation line, and
    an alarm circuit connected to the output of said flow detector for producing an alarm indication if a continuous airflow condition indicative of a cuff leak is detected.

12. The system of claim 11, wherein said flow detector includes a mechanical flow meter in series with said cuff inflation line and sensor means operatively connected to said flowmeter for producing an electrical output signal indicative of airflow in said cuff inflation line.

13. An inflation control system for a tracheal tube cuff connected to a cuff inflation line, comprising
a flow detector in the cuff inflation line for producing an electrical output signal indicative of a cuff or cull line leak, and
an alarm circuit connected to the output of said detector for producing an alarm indication when an airflow condition is continuously detected for a predetermined length of time.

14. The system of claim 13, wherein said flow detector includes a mechanical flow meter in series with said cuff inflation line, and a sensor operatively connected to said flow meter for producing an electrical output signal indicative of airflow in said cuff inflation line.

15. An inflation control system for an inflatable cuff of a tracheal tube connected to a volume ventilator having alternating inspiration and exhalation cycles, comprising
an adjustable pressure relief valve having an inlet and an outlet and a valved exhaust port urged toward the closed condition, and
means substantially continuously connecting the inlet and outlet of said pressure relief valve in series between the cuff and a substantially continuous source of pressurized gas throughout the inspiration and exhalation cycles of the ventilator.

16. The system of claim 15, wherein said pressure relief valve is a PEEP-type valve.

17. The system of claim 15, wherein the tube is connected to an exhalation valve and the volume ventilator having a pulsed exhalation valve drive line, and further comprising
means responsive to the exhalation drive line for occluding said exhaust port of said pressure relief valve whenever the exhalation valve is closed.

18. The system of claim 17, wherein said occluding means includes an inflatable balloon in gaseous communication with the exhalation valve drive line for sealing off said exhaust port of said pressure relief valve when inflated in the same manner as the exhalation valve.

19. The system of claim 18, further comprising a manual 3-way valve connecting said balloon to (1) said exhalation drive line, (2) a source of pressurized gas or (3) the atmosphere.

20. The system of claim 15, further comprising means responsive to cycling of the ventilator for locking the exhaust port of the pressure relief valve closed during the inspiration cycle.

* * * * *

UNITED STATES PATENT AND TRADEMARK OFFICE
CERTIFICATE OF CORRECTION

PATENT NO. : 4,924,862

DATED : May 15, 1990

INVENTOR(S) : Gary Levinson

It is certified that error appears in the above-identified patent and that said Letters Patent is hereby corrected as shown below:

ON THE TITLE PAGE

In the references Cited, "Igrich" should be --Igich-- and "Kowaleski" should be --Kowalewski--.
Column 1, line 44, "intra cuff" should be --intra-cuff--.
Column 3, line 30, "rotameter type" should be --rotameter-type--.
Column 4, line 7, "PEEP type" should be --PEEP-type--;
         line 59, "system)" should be --system.)--.
Column 5, line 5, "2B" should be --28--.
Column 7, line 41, "PEEP type" should be --PEEP-type--.
Column 8, line 5, "PEEP type" should be --PEEP-type--;
         line 45, "PREP-type" should be --PEEP-type--.

Signed and Sealed this

Eleventh Day of February, 1992

Attest:

HARRY F. MANBECK, JR.

*Attesting Officer*      *Commissioner of Patents and Trademarks*